United States Patent [19]
Gabriel et al.

[11] Patent Number: 5,114,406
[45] Date of Patent: May 19, 1992

[54] INJECTION DEVICE FOR INJECTION, ESPECIALLY SELF-ADMINISTERED INJECTION, OF MEDICAMENT, INCLUDING MECHANISMS FOR NULLING AND FOR SELECTING DOSAGE, ESPECIALLY FOR USE WITH MULTI-DOSE AMPULES

[75] Inventors: Jochen Gabriel, Stuttgart; Herbert Bechtold, Ehningen; Gerhard Hambrecht, Rosenberg-Sindolzheim; Klaus Nothdurft, Stuttgart, all of Fed. Rep. of Germany

[73] Assignee: Wilhelm Haselmeier GmbH & Co., Stuttgart, Fed. Rep. of Germany

[21] Appl. No.: 466,999

[22] Filed: Jan. 18, 1990

Related U.S. Application Data

[63] Continuation of Ser. No. 121,192, Nov. 16, 1987, abandoned.

[30] Foreign Application Priority Data

Nov. 14, 1986 [DE] Fed. Rep. of Germany ....... 3638984

[51] Int. Cl.⁵ .............................................. A61M 5/20
[52] U.S. Cl. .................... 604/136; 604/134; 604/156; 604/232; 604/138
[58] Field of Search .............................. 604/134–139, 604/156, 157, 186, 207–209, 211, 218, 201, 228, 232

[56] References Cited

U.S. PATENT DOCUMENTS

| | | | |
|---|---|---|---|
| 159,192 | 1/1875 | Leiter | 604/136 |
| 2,565,081 | 8/1951 | Maynes. | |
| 2,605,766 | 8/1952 | Uytenbogaart. | |
| 3,066,670 | 12/1962 | Stauffer. | |
| 3,101,711 | 8/1968 | Reitknecht | 604/209 |
| 3,330,279 | 7/1967 | Sanoff et al. | 604/138 |
| 3,334,788 | 8/1967 | Hamilton | 604/135 |
| 3,729,003 | 4/1973 | Hurschman. | |
| 3,880,163 | 4/1975 | Ritterskamp. | |
| 4,031,893 | 6/1977 | Kaplan et al.. | |
| 4,194,505 | 3/1980 | Schmitz. | |
| 4,231,368 | 11/1980 | Becker. | |
| 4,592,745 | 6/1986 | Rex et al.. | |
| 4,973,318 | 11/1990 | Holm et al.. | |

FOREIGN PATENT DOCUMENTS

| | | |
|---|---|---|
| 0058536 | 8/1982 | European Pat. Off.. |
| 7204481 | 4/1973 | Fed. Rep. of Germany. |
| 3527066 | 2/1986 | Fed. Rep. of Germany. |
| 3604826 | 10/1986 | Fed. Rep. of Germany. |
| WO85/03446 | 8/1985 | PCT Int'l Appl.. |

OTHER PUBLICATIONS

Insuject ® from Nordisk, Nordisk Gentofte A/S, pp. 535–536.

Primary Examiner—Richard J. Apley
Assistant Examiner—Linda C. M. Dvorak
Attorney, Agent, or Firm—Frishauf, Holtz, Goodman & Woodward

[57] ABSTRACT

To permit accuracy presetting of a dose for an injection to be ejected from an ampule (12) containing more fluid medication than the dose requires, a plunger (18) which is telescopically received within a tubular element (77) is movable against the customary piston (17) in the ampule for a distance which depends on the extent of telescopic insertion of the plunger stem (18″) within the tubular element (77). This extent can be set by a rotary knob or sleeve (56, 65) which rotates the tubular element with respect to the plunger (18); the plunger and tubular element are coupled together by a steeply pitched spiral thread (76), thereby controlling the extent of projection of the combined injection dosing arrangement of plunger (18) and plunger length setting mechanism (77), and hence controlling the amount of medicinal fluid expelled through an injection needle (16) coupled to the ampule (12) at the end of the injection device.

42 Claims, 6 Drawing Sheets

INJECTION DEVICE FOR INJECTION, ESPECIALLY SELF-ADMINISTERED INJECTION, OF MEDICAMENT, INCLUDING MECHANISMS FOR NULLING AND FOR SELECTING DOSAGE, ESPECIALLY FOR USE WITH MULTI-DOSE AMPULES

This application is a continuation of application Ser. No. 121,192 filed Nov. 16, 1987, abandoned.

FIELD OF THE INVENTION

The invention relates to injection devices having a housing to hold a container or ampule which contains medicament to be injected, and more particularly to such devices which are easy to use and permit presetting of a selected injection dosage from an ampule containing sufficient medication for more than one injection.

BACKGROUND

U.S. Pat. No. 4,194,505 discloses an injection device of this type in which the dosage can be selected by the user. This known device is designed to accomodate a special cartridge or ampule. The ampule contains for example a certain amount of insulin, for example 20 units. If the patient needs only 17 units, he can adjust the injection device correspondingly. First, the patient adjusts the injection device for the maximum dosage; to do this, the patient uses a null- or zero-marking on the injection device. Next, the patient adjusts an adjuster for three lines on a scale; this corresponds to the 3 units that the patient does not require (20−27 =3). Then he performs the injection.

This known injection device has two considerable disadvantages:

a) Only adjustment within a very limited range is possible. For example, if the patient requires at one time 28 units of insulin, he can make use of a 30-unit ampule, because the difference of two units is well within the range of adjustability. However, if another time the patient requires 19 units, it is no longer possible to use a 30-unit ampule, and a 20-unit ampule must be used. Therefore, it is necessary to use ampules that contain different quantities, namely different ampules that contain 10, 20, 30, 40, 50 or 60 units. If the patient is blind, he can easily make a mistake and use the wrong ampule. There is then the danger that he will inject too much insulin.

b) The computation and adjustment work involved in utilizing, e.g., a 20-unit ampule to perform a 17-unit injection, is easy for many persons. However, for many other persons this computation and adjustment work is too complicated. For example, with so-called "intensivated insulin therapy", the patient must inject a first amount of insulin after breakfast, a different second amount after lunch, and a different third amount after dinner. An example: The patient needs e.g. 8 units after breakfast, 15 units after lunch, and 12 units after dinner. Therefore, for breakfast the patient must use an ampule containing 10 units and adjust the device to −2 units. For after lunch and for after dinner, he must use an ampule having 20 units. However, for after lunch he must adjust the injection device to −5 units, and for after dinner he must adjust the device to −8 units. This computation and adjustment work requires a certain degree of care and can easily lead to mistakes.

THE INVENTION

It is therefore an object of the invention to avoid the specified disadvantages of the known injection device.

It is a further object to provide an injection device having a structure which can be adjusted to permit injection of a selected dosage from a given ampule.

Briefly, an injection dosing arrangement formed by a plunger and a plunger-lengthening mechanism is provided to control the required dosage upon injection. The plunger-lengthening mechanism includes a steeply pitched spiral coupled to the plunger in such a manner that the combined length of the plunger and plunger-lengthening mechanism is changeable, as set by an adjusting knob or ring for effecting changes of this combined length. This combined length may be changed may be changed, in a variety of ways some of which are disclosed hereinafter, for such purposes as nulling or re-nulling the device, expelling air from a multi-dose ampule, and adjusting different successive dosage values for the medicament to be expelled through the injection needle from a multi-dose ampule or a succession of single-dose ampules.

If desired, the plunger-lengthening mechanism and the adjusting mechanism which controls the combined length of the plunger and plunger-lengthening mechanism can be designed such that the injection device can use an ampule that contains enough medication, e.g. insulin, for several injections. The patient uses the adjusting mechanism to select the respectively required, different dosage values that he needs for morning, for midday, and for evening. The fluid (e.g. insulin) for these different injections comes from only one ampule. In this way, the patient can use one ampule for e.g. 2 or 3 days, before it is necessary to insert a new and full ampule. This is possible with the structure of the invention, because the plunger-lengthening mechanism can make the plunger long enough to enter the ampule just slightly when the ampule is new and full, and then to go considerably deeper into the ampule the second day when the ampule is then partly empty, etc. The possibility of using one ampule for e.g. 2-3 days is a considerable advantage, and no less so in the case of devices and/or applications wherein the dosage is always to be the same.

The use of a plunger-lengthening mechanism or, more precisely, the use of a plunger with a plunger-lengthening mechanism so that the combined length is changeable, provides a number of different forms of adjustability, and possible combinations of adjustability. In the preferred embodiment described herein, the aforementioned combined length is changed in order to null or re-null the injector device when using a multi-dose ampule capable of providing medicament for a considerable number of injections; furthermore, the aforementioned combined length is also changed in order to change the dosage quantities for successive injections. Very advantageously, the nulling or re-nulling process has no influence upon the dosage-establishing means of the device, so that dosage selection is not complicated by the nulling or re-nulling process. Conversely, dosage selection has no influence on, or counteracts the nulling or re-nulling, so that nulling is not complicated by the dosage selection itself. Additionally, the requisite changes in the combined length of the plunger and plunger-lengthening mechanism, which may be of considerable magnitude, have no substantial influence upon the distance by which the injection needle rapidly emerges from the device housing when the drive spring is released.

Clearly, use of the novel combination of plunger and plunger-lengthening mechanism (or more precisely, the possibility of changing the length of that combination) to effect both nulling and dosage selection independently of each other and without influence upon the needle-penetration depth is a dramatic example of the possibilities which are opened up by this broadest concept of the invention.

However, the concept of changing the total length of the combination of plunger and plunger-lengthening mechanism only for nulling or re-nulling purposes, or only for dosage selection, is no less novel and advantageous, because what is in question is a new form of adjustability for such injection devices, even if exploited for only one adjustment and not, as in the preferred embodiment, two adjustments. For example, a form of adjustment often encountered in the prior art adjustment of the stroke-length of the plunger. Accordingly, it is within the scope of the present invention, for example, to change the total length of the combination of plunger and plunger-lengthening mechanism for the purpose of dosage selection, but to change the stroke-length of the combination of plunger and plunger-lengthening mechanism to effect, e.g., nulling, or most especially re-nulling when the injector device accomodates a multi-dose ampule. (It should be immediately noted that changing the total length of the combination of the plunger and plunger-lengthening mechanism is a concept quite distinct from changing the stroke-length of the plunger; for example, abstractly speaking, in the present invention the stroke-length of the plunger can be kept unchanged while e.g. doubling the total length of the combination of plunger and plunger-lengthening mechanism).

Similarly, although the disclosed exemplary embodiment involves two adjustments, both implemented by changing the total length of the combination of the plunger and plunger-lengthening mechanism, a greater number of adjustments could be involved, including for example selection of needle penetration depth.

DRAWINGS

DETAILED DESCRIPTION

Figure 1:
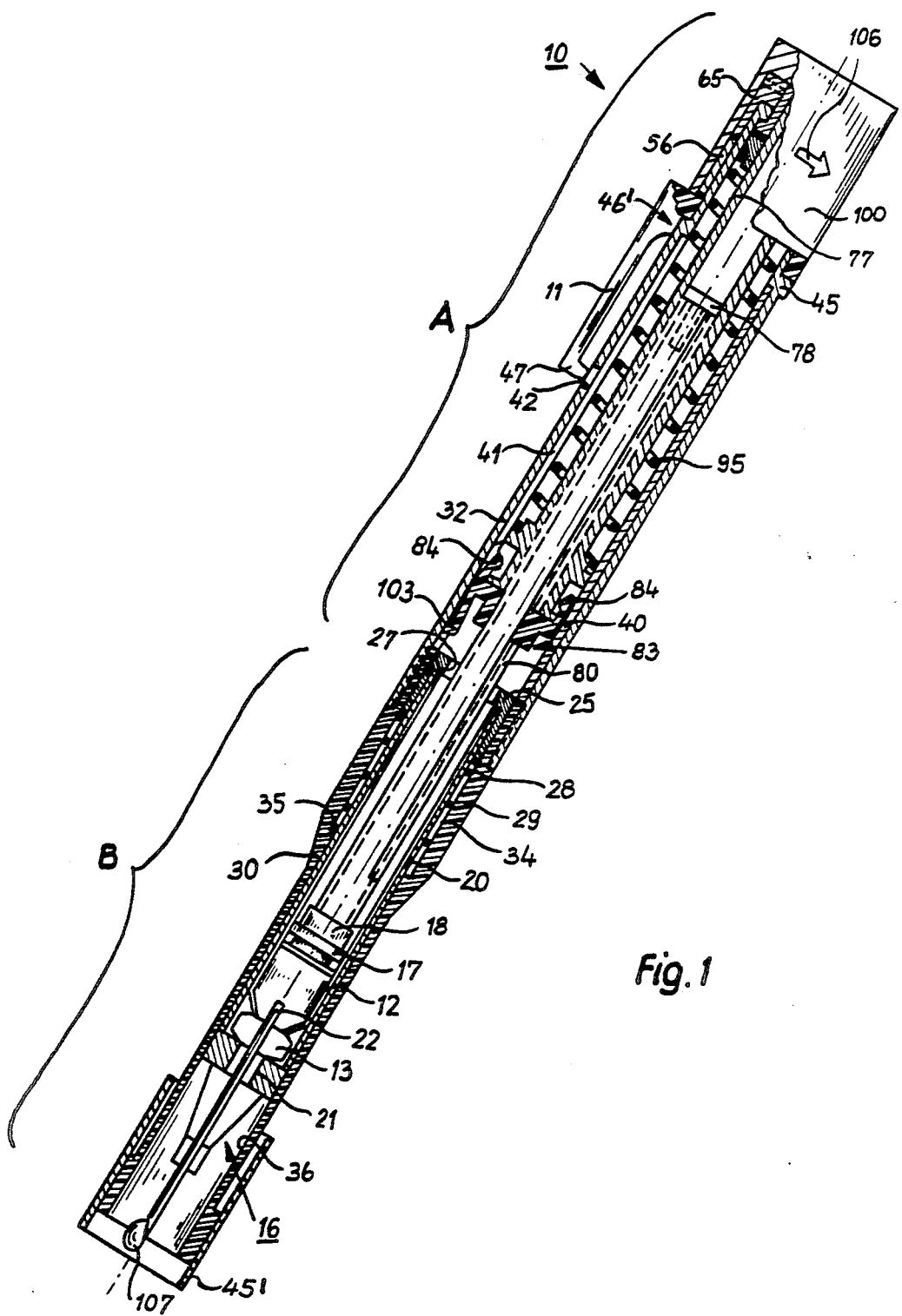
FIG. 1 is a longitudinal section through a preferred embodiment of an inventive injection device, in its not cocked condition; the drawing is on a scale that is bigger than true scale.

FIG. 1 shows the injection device 10 in collapsed, i.e. axially pushed-together state. This is the state of the device after an injection, that is, a rest state, and before the injection device is re-cocked for a next injection. As can be seen, a drive spring 95, which is a compression spring, is not greatly compressed.

The injection device 10 has approximately the shape of a large fountain pen. It has on its side an attachment clip 11 of the shape known from fountain pens; this clip 11 also serves as the trigger element for the injection. In a manner explained below, when the patient presses clip 11 inwardly, a spring-driven injection is initiated and performed.

Figure 4:
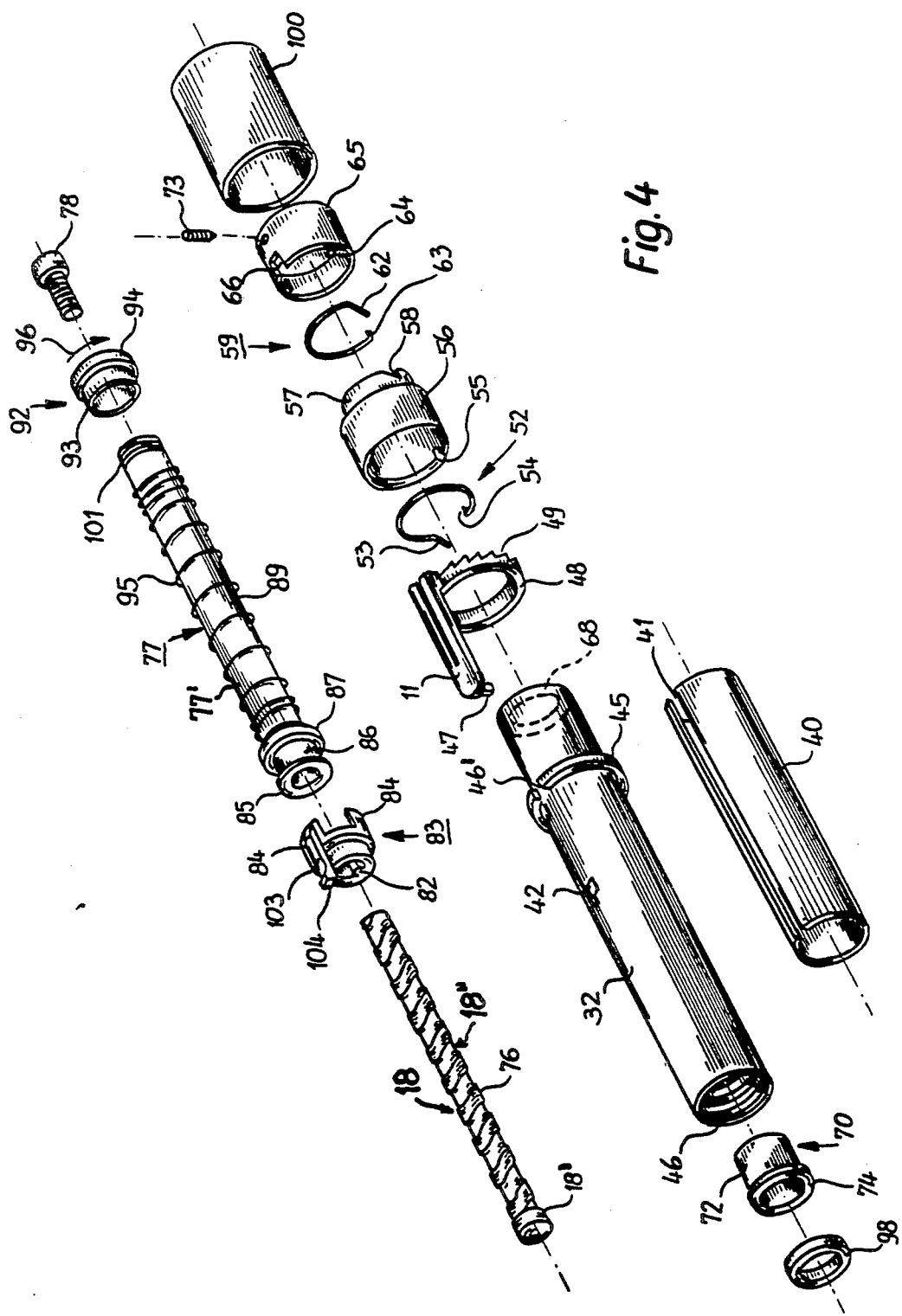
FIG. 4 is an exploded view of part A of the injection device, part A being the part that contains the drive spring and the different mechanisms for adjusting the injection operation of the device and for selecting dosage.
Figure 5:
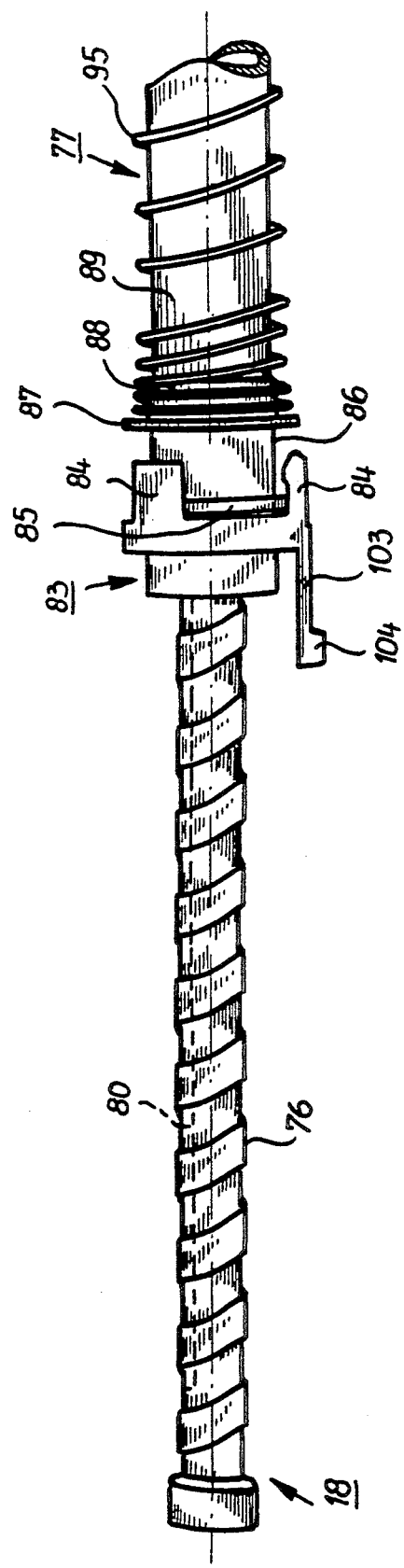
FIG. 5 shows the plunger, part of the plunger-lengthening mechanism, and also the guidance element which is secured to these two components; the plunger has an external thread, with for example 8 mm pitch, i.e. between successive turns of the thread; and the thread has a rectangular cross section.

The injection device 10 has a part A which contains the mechanisms which adjust the volume of fluid medication to be injected and which produce the axial force to perform the injection. FIG. 4 shows the elements of part A disassembled, to facilitate visualization. FIG. 5 depicts an important portion of part A in the form of a realistic or three-dimensional picture.

Figure 3:
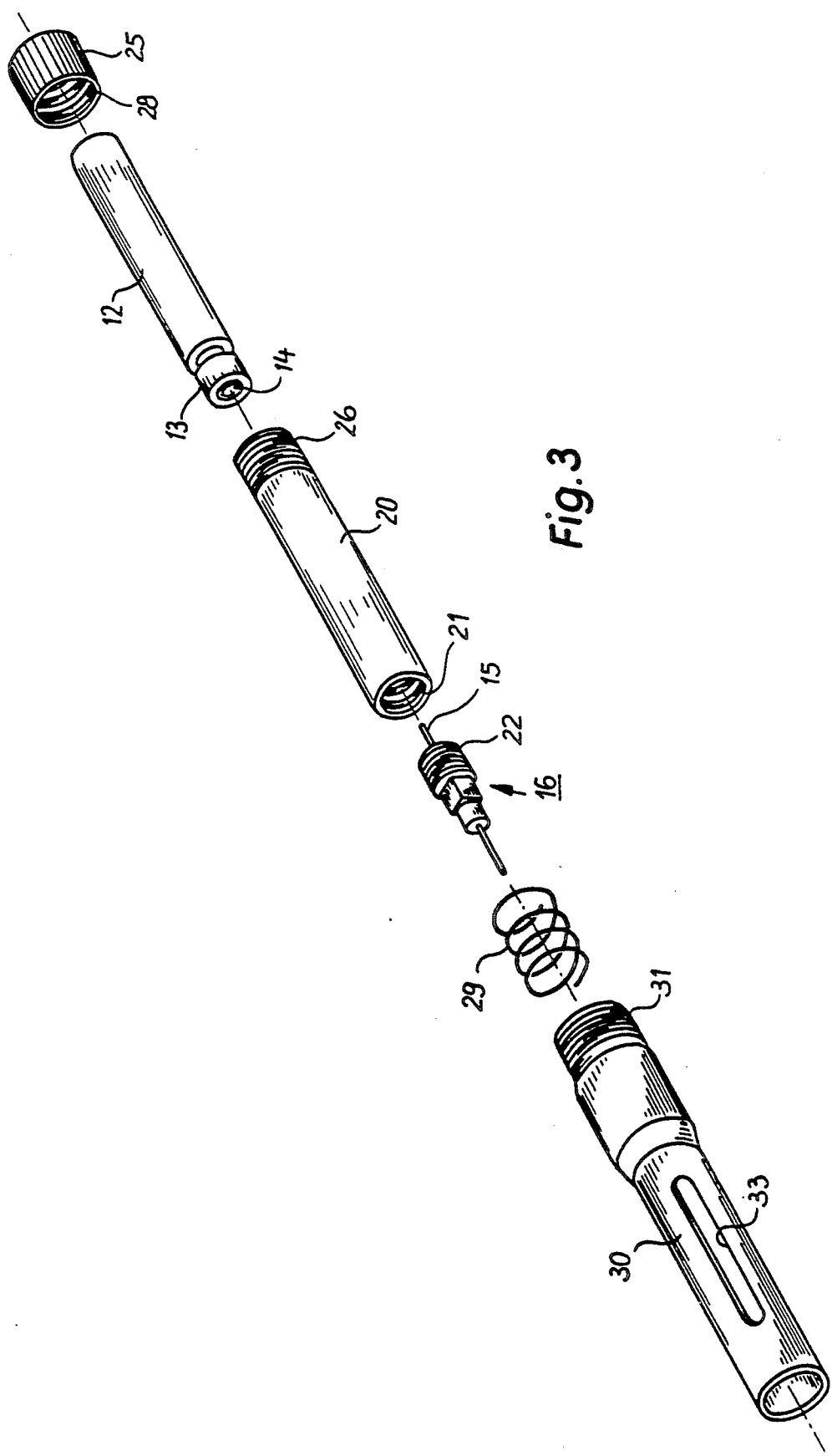
FIG. 3 is an exploded view of part B of the injection device, part B being the part that accomodates the medicament-containing, multi-dose ampule.

Part B of the injection devices accomodates an ampule 12 which, however, will be referred to herein as "container 12"; container 12 contains the medicament to be injected. FIG. 3 shows the elements of part B disassembled, again to facilitate visualization.

As shown in FIGS. 1 and 3, container 12 is a somewhat long, cylindrical, small glass tube; this tube is smaller at its proximal end, i.e. at the end that is near to the patient. Container 12 has an aluminum cap 13. A thin rubber diaphragm 14 is mounted in the cap 13. The injection needle 16 has a distal end 15, i.e. the end that is not near to the patient. The distal end 15 of needle 16 pierces the thin rubber diaphragm 14, and therefore can enter into the interior of container 12. Such containers, filled with insulin, are e.g. marketed by the firm Novo Industri AB, of Denmark, under the mark "Penfill". The small glass tube 12 retains a shiftable piston 17 which e.g. can be made of a suitable rubber. A plunger 18 can move the piston 17 in the proximal direction (in the direction of the patient), to perform an injection.

A container-holding sleeve or housing 20 accomodates container 12. Sleeve 20, at its proximal end, has an internal thread 21. Thread 21 receives the external thread 22 of the injection needle element 16 (see FIG. 3). Container 12 contains enough fluid for several injections, e.g. a total of 100 units of insulin. After one injection, it is necessary to use a new and sterile needle 16. The old needle 16 is screwed out from the thread 21, and the distal end 15 of needle 16 exits the thin rubber diaphragm 14. Diaphragm 14 is self-sealing. Thus, when the old needle is removed, diaphragm 14 is again in sealed state, and can protect the medicament container 12. Then, the new needle 16 is screwed into thread 21.

A threaded cap 25 (see FIG. 3) closes the distal end of container-holding sleeve 20. Threaded cap 25 has a peripheral surface which is knurled, to help the fingers of the user turn the cap 25. Threaded cap 25 is screwed onto an external thread 26 at the distal end of the container-holding sleeve 20. Cap 25 has a central opening 27 (FIGS. 1 and 2), and plunger 18 can move easily in the axial direction through this opening 27. Cap 25, at its proximal end, has a shoulder 28. Shoulder 28 forms a surface which supports one end of a needle-return spring 29. Container-accomodating sleeve 20 is advantageously made from a transparent plastic, so that the patient can see whether container 12 is, for example, very full or almost empty.

An important feature of the illustrated exemplary embodiment is this: Container-holding sleeve 20 can have a shape which very exactly corresponds to the shape of the container 12 from a particular manufacturer. As a result, it is not possible to use a wrong container with a higher dosage; to use a wrong container with a higher dosage of (for example) insulin, would be dangerous; if the patient injects too much insulin, the patient could fall into a coma.

Figure 2:
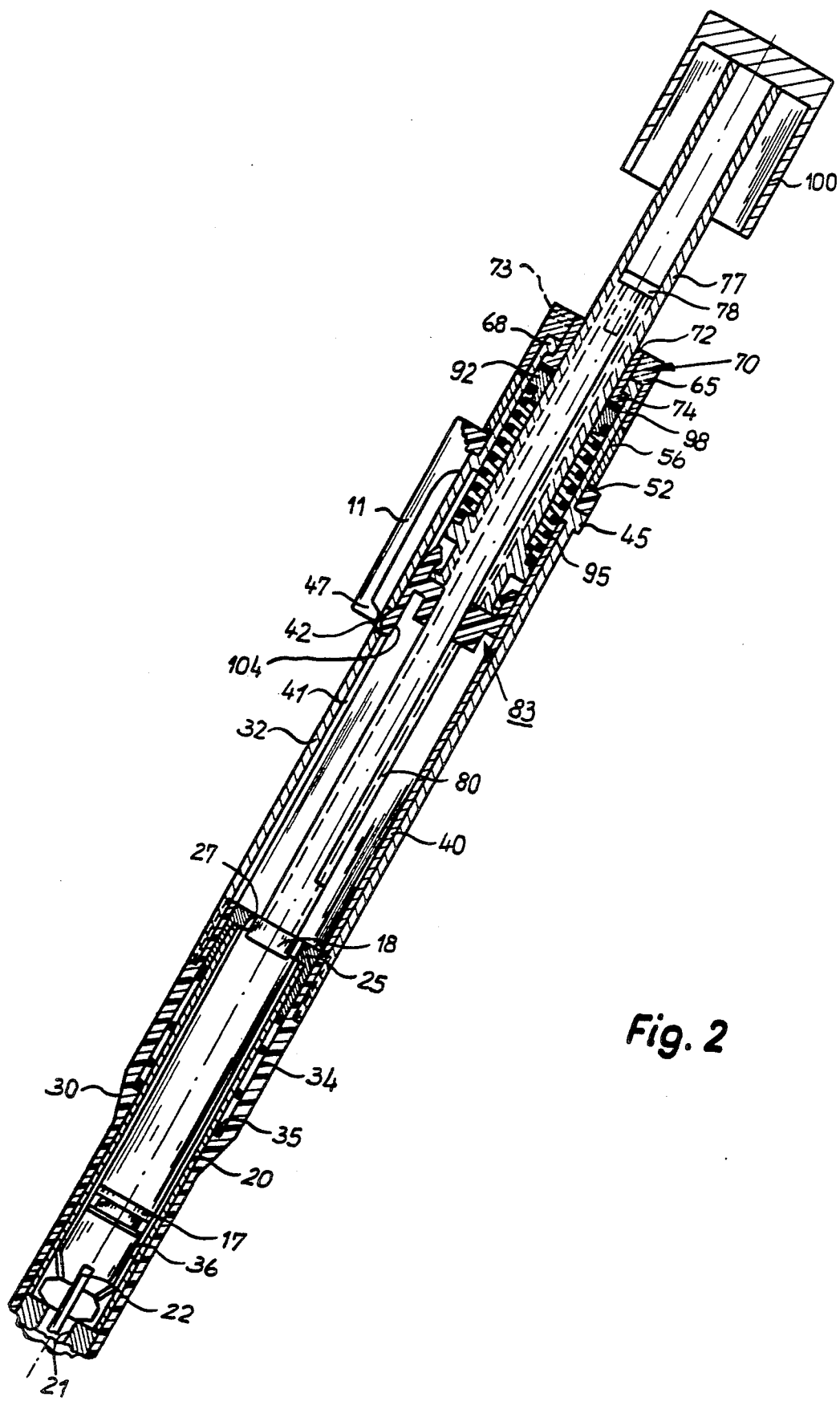
FIG. 2 illustrates a part of the injection device of FIG. 1, but here the drive spring at the upper end of the injection device is in its cocked condition.

The injection device has, in portion B, a proximal exterior housing part 30 (FIG. 3) and, in portion A, a distal exterior housing part 32 (FIG. 4). The rear end of proximal housing part 30 has an external thread 31 (FIG. 3). The front end of distal housing part 32 has an internal thread 46 (FIG. 4). External thread 31 is screwed into internal thread 46, to form the complete exterior housing 30, 32 of the injection device. The proximal housing part 30 (FIG. 3) contains the needle-return spring 29, the needle 16, and the container-holding sleeve 20; the container-holding sleeve 20 accomodates the container 12; and the screw cap 25 holds the container 12 in the sleeve 20. Proximal housing part 30 (FIG. 3) has a window 33, so that the patient can see through sleeve 20 and into the transparent container 12. The proximal housing part 30 can be manufactured from metal, e.g. aluminum, or from a suitable synthetic plastic, e.g. polypropylene. As FIGS. 1 and 2 show, the proximal part 30 of the exterior housing has a cylindrical rear chamber 34 of larger diameter, and a cylindrical front chamber 36 of smaller diameter; this can also be seen, exteriorly, in FIG. 3. As seen in FIGS. 1 and 2, an annular shoulder 35 is formed between chambers 34 and 36. The diameter of chamber 36 is a little greater than the outer diameter of container-holding sleeve 20, so that sleeve 20 can move axially in chamber 36. The front end of needle-return spring 29 (FIG. 3) presses against shoulder 35. The rear end of spring 29 presses against the annular shoulder 28 (FIG. 3) of the screw cap 28. Therefore, the spring 29 always tries to push the screw cap 25 away from the shoulder 35, i.e. in the distal direction. In other words, the needle-return spring 29 always tries (FIG. 3) to push back the combination of the needle 16 and the container-holding sleeve 20 (and of course the container 12 in sleeve 20). FIGS. 1 and 2 depict spring 29 at zero or minimum compression, and at full or maximum length. If spring 29 has zero compression and full length, the rear end of screw cap 25 is in the axial position shown, i.e., at the same axial position as the front end of a sleeve 40, as seen in FIGS. 1 and 2. Sleeve 40 is also shown in FIG. 4. It can happen that different springs 29 have different lengths, or that their relaxed length changes after, for example, some months of use. Therefore, it is alternatively possible to provide a radially inward shoulder at the proximal end of sleeve 40. If that is done, spring 29 cannot push the elements 16+20+12+25 farther back than the proximal end of sleeve 40. Accordingly, if sleeve 40 is provided with such a shoulder, spring 29 can have a maximum length with minimum compression, but cannot have its full length with actually zero compression.

As already said, in the FIG. 1 situation, return spring 29 is at zero or minimum compression, the elements 16+20+12+25 being in the positions shown, i.e., the distal end of screw cap 25 being at the same axial position as the proximal end of sleeve 40.

As shown in FIG. 4, sleeve 40 has a longitudinal slit 41. In a manner described below, slit 41 longitudinally guides plunger 18 and also prevents plunger 18 from rotating. Sleeve 40 is secured, e.g. press-fitted inside the distal part 32 of the exterior housing of the device. Also, slit 41 has the same angular position as a window 42 in the distal housing part 32.

FIG. 3 depicts, in disassembled condition, the B-part of the injection device. The B-part is assembled as follows: First, a fresh container 12 is pushed into container-holding sleeve 20. Next, screw cap 25 is screwed onto external thread 26. Then, a fresh injection needle 16, with its external thread 22, is screwed into the internal thread 21 of sleeve 20. It will be understood that, in conventional manner, the needle is purchased with a (not illustrated) protector, for example made of clear plastic. The protector covers needle 16 and keeps it clean. The protector makes it possible to hold the needle in one's hand and screw it into thread 21, without contamination. The distal end 15 of needle 16 pierces through thin rubber diaphragm 14 and enters the body of medicament in container 12. Next, container-holding sleeve 20 is pushed into the rear end of proximal housing part 30. The outer diameter of screw cap 25 is smaller than the inner diameter of chamber 34 of proximal housing part 32, so that screw cap 25 likewise can be pushed into proximal housing part 30. Spring 29 is already inside the chamber 34 of housing part 30. To protect injection needle 16, housing part 30 has, at its proximal end, a cylindrical protection-sleeve 45' (FIG. 1) or a (not shown) cup-shaped protective cap. The proximal part 30 of the exterior housing of the device is now loaded. Next, housing part 30, with its thread 31, is screwed into the thread 46 (FIG. 4) of the distal part 32 of the exterior housing. The injection device is now ready to perform several injections, e.g. in accordance with so-called "intensivated insulin therapy". If the patient needs, e.g., a first dosage in the morning, a different second dosage at mid-day, and a different third dosage in the evening, this can be implemented. How this is implemented will be explained below, after further description of the A-part of the injection device 10.

As already noted, the outer diameter of screw cap 25 is smaller than the inner diameter of the chamber 34 of Proximal housing part 30. Therefore, the combination of the container-holding sleeve 20+the injection needle 16+the screw cap 25 can be shifted in the proximal direction, i.e., against the force of retraction spring 29, until the compression of spring 29 is maximum. As explained in greater detail further below, this type of shifting occurs during an injection, so that needle 16 can move forward out of the front housing part 30 and enter into the tissue of the patient.

As-already observed, sleeve 40 is secured in rearward housing part 32, and its slit 41 registers with the window 42 of housing part 32.

Housing part 32 has, near its distal end, an external ring 45. Ring 45 has an interruption 46' at the same angular position occupied by window 42. The interruption 46' receives a clip 11. When the device is completely assembled, the end of the clip registers with window 42 (see also FIGS. 1 and 2).

Figure 6:
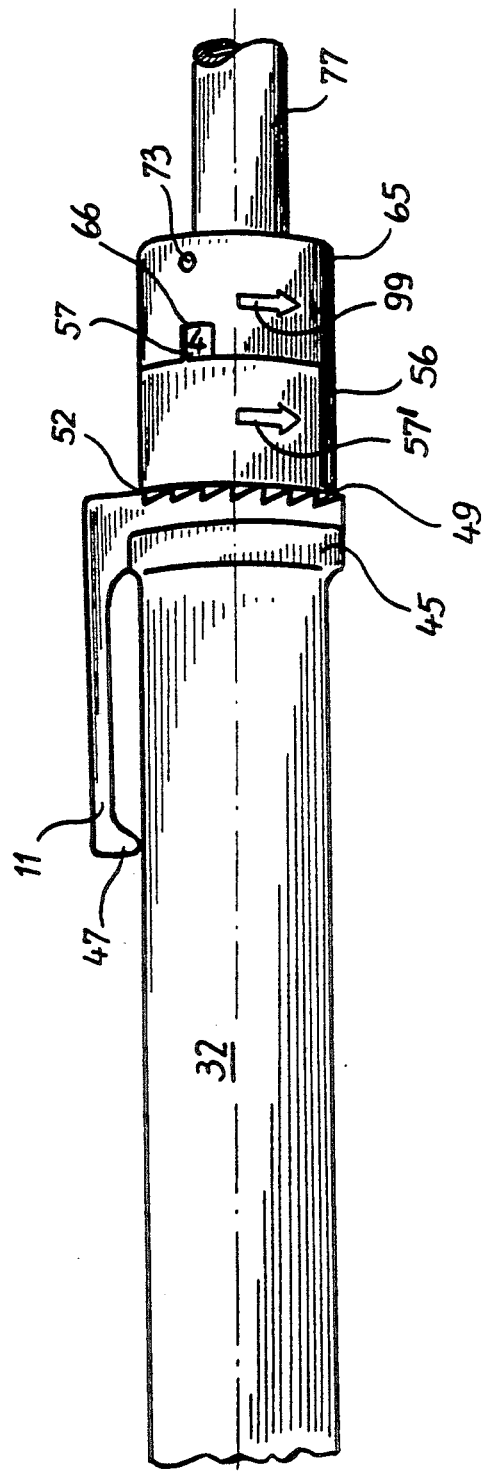
FIG. 6 is a pictorial view of a preferred exemplary embodiment of the adjustment arrangement that the patient uses to adjust the dosage of fluid to be injected.

Clip 11 can e.g. be designed as an injection-molded element made of polyamide. Clip 11 has a holding ring 48, which at its distal side has sawtooth-like ratchet teeth 49 (FIG. 6). These teeth 49 are inclined in a direction opposite to arrow 96 (FIG. 4), or—the same thing—opposite to the arrows 57 and 99 in FIG. 6.

After the holding ring 48 of claim 11, proceeding distally, there is a springy ring 52. The left end of springy ring 52 (as viewed in FIG. 4) is bent into the proximal direction, to form a ratchet pawl 53 to cooperate with the ratchet teeth 49. The right end of springy ring 52 (as viewed in FIG. 4) has a portion 54 which is bent perpendicular into the distal direction. Bent end 54 engages in an axially extending recess 55 in the proximal end of a pre-selector wheel 56. Pre-selector wheel 56 is rotatably mounted on the distal end of distal housing part 32. Because bent end 54 is received in recess 55, pre-selector wheel 56 can rotate only in the direction of arrow 57 (FIG. 6).

Pre-selector wheel 56 has a portion 57 of reduced diameter. Portion 57 carries a dosage adjustment scale, e.g. in the form of a series of numerals, symbolically indicated in FIG. 6 by the numeral "4".

As shown in FIG. 4, the distal end portion 57 has a sawtooth-shaped recess 58. A springy ring 59 has a right end 62 which is bent at an angle in proximal direction and engages in this recess 58. The left end 63 of springy ring 59 is bent at a right angle into the distal direction. This left end 63 engages in an axial hole 64 of an adjusting element 65. Adjusting element 65 is rotatably mounted on the scale portion 57 of pre-selector wheel 56. Adjusting element 65 has a window 66 through which individual ones of the different numerals of the scale on portion 57 can be viewed.

The distal part 32 of the exterior housing has, at its distal end, a radially inward shoulder 68 (see FIG. 4, also FIG. 2). Shoulder 68 serves as a stop for a first flanged sleeve 70. Flanged sleeve 70 has a cylindrical portion 72 and, at its proximal end, a radial ridge or flange 74. Cylindrical portion 72 projects through an opening within shoulder 68 at the distal end of housing part 32 (see also FIG. 2). The adjusting member 65 is mounted on the distal end of distal housing part 32 (FIG. 4, but see also FIG. 2 and FIG. 6). A lock screw 73 (FIG. 4) holds adjusting member 65 on the cylindrical portion 72 of flanged sleeve 70, so that adjusting member 65 and flanged sleeve 70 must always rotate together. The radial flange 74 on said first flanged sleeve 70 abuts against the proximal side of shoulder 68. In this way, adjusting member 65 is mounted at the distal end of housing part 32 for rotation relative to the same.

The plunger 18 has a stem 18" formed with an external and steep thread 76, shown in FIG. 4 and also very clearly in FIG. 5. Plunger 18 is guided in a corresponding internal thread of a tubular element 77' forming part of a plunger lengthening arrangement 77, not visible in the figures. Rotation of plunger 18 relative to plunger-lengthening arrangement 77 causes the total length of the combination of components 18+77 to increase or decrease. In other words, the effective length of plunger 18 increases or decreases.

Plunger stem 18" is screwed into an inner thread of tubular element 77' of the plunger-extending arrangement or mechanism 77. A limit screw 78 is screwed into an internal thread in the distal end of the tubular element. When components 18 and 77 are rotated relative to each other in one direction, plunger 18 increasingly emerges from the proximal end of plunger-lengthening mechanism 77. In a manner described below, limit screw 78 limits the total length of the plunger 18 +the plunger-lengthening mechanism 77, so that the plunger 18 cannot move too far in the proximal direction and escape the plunger-lengthening mechanism 77.

Plunger 18 has, at its outer surface, a longitudinal slot or groove 80, seen most clearly in FIGS. 1 and 2. Slot or groove 80 extends almost to the proximal end of plunger 18. Slot 80 receives a radially inward projection 82 of a longitudinal-guidance element 83, best shown in FIG. 4.

In the illustrated embodiment, the longitudinal-guidance element 83 has several functions. Guidance element 83, at its distal end, has three finger-like projections 84. The finger-like projections 84, like a claw, grip over an annular ridge or flange 85 at the proximal end of plunger-lengthening mechanism 77. In other words, the finger-like projections 84 project radially inwardly into the space 86 between the annular flange 85 and a further annular ridge or flange 87. In this way, the plunger-lengthening mechanism 77 and the longitudinal-guidance element 83 can rotate relative to each other; but the elements 77 and 83 cannot move axially relative to each other; when element 77 moves axially element 83 must move axially, and vice versa. Longitudinal-guidance element 83 is advantageously made of an elastic synthetic plastic, e.g. a polyamide; therefore, its finger-like projections 84 can be moun ed on the annular ridge 85 with a simple snap-action.

After the annular ridge 87, proceeding distally, plunger-lengthening mechanism 77 has a smaller-diameter cylindrical portion 89, as seen in FIG. 4. Between annular ridge 87 and cylindrical portion 89, there is a short cylindrical portion 88 (see e.g. FIG. 5) of a diameter greater than the diameter of cylindrical portion 89. The first flanged sleeve 70, associated with part B, has already been mentioned. A second flanged sleeve 92 is arranged axially shiftable on the long cylindrical portion 89 of plunger-lengthening mechanism 77. This second ridged or flanged sleeve 92 has it its proximal end a cylindrical portion 93, and at its distal end an annular ridge or flange 94.

A coil spring 95 is arranged on the plunger-lengthening mechanism 77 and loosely surrounds the cylindrical portion 89. The proximal end of coil spring 95 is tightly pushed onto—and thereby-attached at—the larger-diameter portion 88 at the Proximal end of cylindrical portion 89 (see e.g. FIG. 2). The distal end of coil spring 95 is tightly pushed onto—and thereby attached at—the cylindrical portion 93 of the second flanged sleeve 92.

Coil spring 95 extends from the proximal end to the distal end of plunger-lengthening mechansim 77 with a winding direction indicated by arrow 96 in FIG. 4; see also FIG. 5. The coil spring is the drive spring for the injection device. Thus, it has a dual function; it acts as an operating spring and it is a unidirectional rotary coupling between the plunger-lengthening mechanism 77 and the second ridged sleeve 92. If second ridged or flanged sleeve 92 is rotated in the direction of arrow 96, coil spring 95 transmits this rotation to plunger-lengthening mechanism 77; as a result, elements 92 and 77 together rotate in the direction of arrow 96. If the second flanged or ridged sleeve 92 is rotated opposite to the direction of arrow 96, coil spring 95 does not transmit this rotation to plunger-lengthening mechanism 77; as a result, sleeve 92 rotates but the plunger-lengthening mechanism 77 does not rotate.

When the injection device 10 is completely assembled, a coupling 98 is located between the flange 74 of the first ridged or flanged sleeve 70 and the flange 94 of the second sleeve 9; see FIG. 2 where this is very clearly shown. In the illustrated embodiment, coupling 98 is a simple O-ring which acts as a slip coupling or slip clutch. (Of course, more complicated clutches or couplings can also be used; and the clutch or coupling can be of a different type, i.e., not of the slip-type). Coupling 98 permits the earlier-mentioned adjusting member 65 (FIG. 4) to turn in the direction of the arrow 99 in FIG. 6; this is the same direction as arrow 96 in FIG. 4. When adjusting member 65 is rotated in this direction, the rotation of member 65 is transmitted to first flanged sleeve 70, from there to coupling 98, from there to second flanged sleeve 92, from there to coil spring 95, and from there to plunger-lengthening mechanism 77. The set or lock screw 73 holds adjusting members 65 on the cylindrical portion 72 of first ridged sleeve 70. When plunger-lengthening mechanism 77 turns in this way in the direction of arrow 96, the plunger increasingly emerges from the proximal end of plunger-lengthening mechanism 77. If Plunger 18 moves out the maximum distance from the proximal end of plunger-lengthening mechanism 77, further proximal movement of plunger 18 is prevented by the limit screw 78 at the distal end of the plunger. When the total length of the plunger 18 + the plunger-lengthening mechanism 77 reaches the maximum value, the head of limit screw 78 contacts the internal threads of the plunger lengthening mechanism 77. As a result, plunger 18 cannot move further in the proximal direction, and therefore cannot escape the plunger-lengthening mechanism 77. FIG. 5 shows the maximum distance that plunger 18 can emerge from the proximal end of plunger-lengthening mechanism 77. After this, if adjusting member 65 were to be turned further in direction 96 (FIG. 4) or 99 (FIG. 6), coupling element 98 would commence to slip and, whereas the first flanged sleeve 70 would be able to turn further, the second flanged sleeve 92 would not be able to do so.

A handgrip 100 is screwed onto an external thread 101 (FIG. 4) at the distal end of plunger-lengthening mechanism 77. When the patient pulls handgrip 100 in the disal direction, drive spring 95 becomes compressed. Spring 95 becomes compressed because the proximal end of spring 95 (attached to the proximal end of plunger-lengthening mechanism 77) is pulled in the distal direction, but the distal end of spring 95 cannot move in the distal direction because it is attached to second ridged sleeve 92, which cannot move in the distal direction (see, e.g., FIG. 2). The longitudinal-guidance element 83 is connected to the proximal end of plunger-lengthening mechanism 77; therefore, also the guidance element 83 moves in the distal direction when the handgrip 100 is pulled in the distal direction.

Longitudinal-guidance element 83, at its outer side, has a springy pawl portion 103. Pawl 103 can move axially in the longitudinal slit 41 of sleeve 40. As a result, guidance element 83 can move axially but cannot rotate. Also, threaded plunger 18 cannot rotate, because the non-rotatable guidance element 83 has a radially inward projection 82, and projection 82 is received in the longitudinal surface groove 80 of plunger 18 (see e.g. FIG. 2). The free end of the pawl portion 103 of guidance element 83 has a click nose 104. The handgrip 100 is pulled in the distal direction a sufficient distance, click nose 104 falls into the window 42 of the rear part 32 of the exterior housing 30, 32 of the injection device. As a result, the injection device is now cocked. The cocked state of the injection device is shown in FIG. 2. If now the user presses clip 11 radially inward, the end portion 47 of clip 11 pushes click nose 104 out of window 42. As a result, longitudinal-guidance element 83 is now free to move axially. As a result, drive spring 95 rapidly pushes the distal end of Plunger-lengthening mechanism 77 as well as longitudinal guidance element 83 and plunger 18 in the proximal direction. However, before the user presses clip 11 radially inward in this way, he should make certain adjustments, which are described below.

OPERATION, in general

An ampule, or medication container, is placed in portion B (FIG. 1) by unscrewing part 30 of portion B from part 32 of portion A. Cap 25, pushed outwardly by spring 29, is then accessible, can be removed from sleeve 20, and an ampule inserted, replacing cap 25. A needle can be inserted in the ends by screwing in a needle assembly 16, thereby penetrating through seal 14 of the ampule.

The injection needle 16 is maintained in sterile condition, and the customarily provided end cap can be used to screw the assembly of the needle into the end of the sleeve 20 without contamination.

The portion 30 is now loaded and by connecting thread 31 with thread 46 of the sleeve 32 of portion A, the injection system is ready for an injection.

The hand grip 100 is then rotated in the direction of the arrow 106 (FIG. 1) to screw out the previously retracted plunger 18 from the extension arrangement 77 until the plunger, by pressing against the piston element 17 within the ampule, expels a drop 107 from the tip of the needle 16. This expels any remanent air and indicates to the user that the plunger is properly in engagement with the piston 17. Sleeve 20 and needle 16—see FIG. 1—are shifted in proximal direction, and spring 29 is compressed.

The hand grip 100 is then pulled outwardly the injection device, in distal direction. This stresses spring 95. The nose 104 will snap into window 42 to hold the injection device in cocked poistion, see FIG. 2. The hand grip 100, in this movement, also releases the dosage adjustment position. Sleeve 20 will shift into the position shown in FIG. 2 under influence of the spring 29. The assembly 18 and 77 retracts.

The preselector wheel or dosage selector 56 is rotated in the direction of the arrow 57' until the desired dosage appears in window 66; FIG. 6 illustrates four units. The spring 52 will click over the teeth 49 (FIG. 1) and, at each tooth, provides a snap movement, so that a visually impaired or blind person can count the clicks and thus set the proper dosage. The element 65, containing the window 66, is held stationary via spring 95 and coupling 98 (FIG. 2), that is, does not rotate. The end 62 of spring 59 (FIG. 4) will screw out of the recess 58 of distal end portion 57 of selector wheel 56.

The user now rotates knob 65 in the direction of the arrow 99 (FIG. 6). The coupling element or clutch 95, as well as the spiral spring 95, now cause a corresponding rotation of the plunger-lengthening mechanism 77, which causes the plunger 18 to project from the sleeve portion of the plunger-lengthening mechanism by the amount corresponding to the injection quantity selected. Effectively, the overall length of the sleeve portion 77 and plunger 18 is increased, in accordance with the selected injection quantity.

Movement of the adjusting member 65 in the direction of the arrow 99 is stopped when the spring 59 again snaps into the recess 58 of extending portion 57 of adjusting sleeve 56, thus blocking further rotation of element 66. The patient can now engage the injection apparatus on the body, press in clip 11 which releases spring 95 and with it element 77 and plunger 18.

In essence, therefore, the adjusting ring 56 sets the rotary position about which member 65 can then be rotated to project plunger 18 from the plunger-lengthening mechanism 77.

When assembled, the return spring 29 is positioned between the ring shoulder 28 on the cap 25 and the ring shoulder 35, and thus biasses the ampule 20 in distal direction. The position of the device, immediately after an injection, is such that the spring 29 is stressed, that is, the injection needle 16 is pushed forwardly, with reference to FIG. 1, and the plunger 18 is in engagement against the piston 17 and prevents relaxation of the spring 29. The plunger 18 is retracted again in advance of the next injection by pulling the hand grip 100 outwardly. As seen in FIG. 2, spring 29 will thus relax and press the ampule or container 20 in distal direction to the abutment against sleeve 40 in portion A, see FIG. 4.

OPERATION, details (1) Let it be assumed that the patient has been given an injection. (The particulars of the injection are described further below).

(2) After this injection, for example, container 12 is now empty or almost empty. The patient unscrews proximal housing part 30 from distal housing part 32, and manually extracts the empty container 12. Then, in the way already described, the patient inserts a new and full container 12 into the B-part of the injection device.

However, it is too early to re-connect the proximal housing part 30 to the distal housing part 32.

(3) Next, the patient rotates the handgrip 100 opposite to the direction of arrow 96 (FIG. 4) or—the same thing—opposite to the direction of arrows 57', 99 (FIG. 6).

As already noted, handgrip 100 is directly screwed to the distal thread 101 of plunger-lengthening mechanism 77. Therefore, the plunger-lengthening mechanism also rotates opposite to the direction of arrow 96 (FIG. 4).

As a result, plunger 18 slowly telescopically retracts as much as possible into the proximal end of plunger-lengthening mechanism 77. Therefore, the total length of the plunger 18+the plunger-lengthening mechanism 77 is now minimum.

During this rotation of handgrip 100 opposite to arrow 96, the second flanged sleeve 92 does not rotate. The flanged sleeve 92 and the plunger-lengthening mechanism 77 can rotate together only in the direction of arrow 96, due to the action of drive spring 95 as a unidirectional rotary coupling. Therefore, during this rotation of handgrip 100 opposite to arrow 96, the first flanged sleeve 70 likewise fails to rotate. Consequently, adjusting member 65, connected by screw 73 to sleeve 70, does not rotate. Also, pre-selector wheel 56 connected to adjusting member by spring 57 does not rotate.

(4) Next, the patient screws the proximal housing part 30 into the distal housing part 32. Now, the two housing parts 30, 32 are connected again.

(5) Next, the patient rotates handgrip 100 in the direction of arrow 96 (FIG. 4) or —the same thing—in the direction of arrows 51', 99 (FIG. 6).

As a result, plunger-lengthening mechanism 77 now rotates in the direction of arrow 96.

Therefore, plunger 18 slowly emerges from the distal end of plunger-lengthening mechanism 77. The total length of 18+77 becomes greater and greater.

Finally, the proximal end, that is, the plunger head 18' of plunger 18 contacs the distal side of piston 17. (This is shown in FIG. 1. However, FIG. 1 does not show a new and full container 12. In FIG. 1, the container 12 is less than 50% full).

Although the action of drive spring 95 as a unidirectional coupling permits plunger-lengthening mechanism 77 and second ridged sleeve 92 to turn together in the direction of arrow 96, it does not at this stage of operation follow that the first ridged or flanged sleeve 70 is carried along. At this stage of operation, the compression spring 95 is relatively uncompressed (see FIG. 1). Accordingly, its distal end (see FIG. 1) does not press hard in distal direction against second ridged or flanged sleeve 92. As a result, the O-ring like slip coupling 98, axially intermediate second ridged sleeve 92 and first ridged sleeve 70, is not axially pressed together by the two sleeves 92, 70 with any significant axial force. Accordingly, ridged sleeve 92 simply slips relative to the presently non-rotating ridged sleeve 70. As earlier noted, adjusting member 65 is directly secured to sleeve 70 by lock screw 73. Therefore, adjusting member 65 likewise fails to rotate. Similarly, pre-selector wheel 56, connected to adjusting member 65 by spring 59, does not rotate at this time.

(5a) Next, handgrip 100 is turned in the direction of arrow 96 a smal further distance. As a result, one drop 107 of fluid emerges from the proximal end of needle 16. Accordingly, the patient is now informed that this part of the adjustment is completed. This establishes a "zero" or null length for the combination of elements 18 +77 in dependence on quantity of medication in container 20.

(6) The handgrip 100 is then pulled in distal direction. This compresses spring 95 (as shown in FIG. 2). When pawl nose 104 snaps into window 42, the injection device is cocked; drive spring 95 is locked in the compressed state of FIG. 2.

(7) See FIG. 6. The numeral (in FIG. 6 the numeral is shown as "4") on the scale 57', seen through the window 66, is now a "0" (i.e. zero). Why this is so will be xplained further below.

(8) Next, the patient rotates pre-selector wheel 56 (FIG. 6), so that a numeral equal to or corresponding to the desired dosage value moves into window 66. For example, the desired dosage may be four units, and the patient wants the numeral "4" to appear in window 66, in the way shown in FIG. 6.

When the patient rotates pre-selector wheel 56 in this way, spring 52 (FIG. 4) at its left end 53 moves over the teeth 49. Spring 52 produces a first clicking noise when the numeral in window 66 changes from "0" to "138 , then again produces a clicking noise when the numeral in window 66 changes from "1" to "2", then a noise from "2" to "3", and a noise from "3" to "4". In this way, a blind patient can count the clicking noises; four clicking noises informs the patient that the numeral in window 66 is now a "4".

Advantageously, the noise-producing spring 52 can be relatively stiff and strong. A first advantage is this: the noise produced when the left end 53 of spring 59 falls down the steep side of each tooth 49 will be loud and easy to hear. A second advantage is this: The pre-selector wheel 56 will be somewhat difficult to rotate; therefore, the patient cannot rotate the pre-selector wheel too fast, e.g., before remembering to count the noises. If the pre-selector wheel 56 is a little difficult to rotate, the patient will give more attention and concentration to this adjustment.

When the patient rotates pre-selector wheel 56 in this way, the right end 62 of spring 59 slides out of the notch 58 of pre-selector wheel 56. Therefore, during this rotation of wheel 56, spring 59 does not connect wheel 56 to adjusting member 65. As a result, member 65 does not rotate and, similarly, plunger-lengthening mechanism 77 does not rotate. To repeat, spring 59 does not connect wheel 56 to adjusting member 65 during this rotation. However, it can happen that there might be some little frictional contact between pre-selector wheel 56 and adjusting member 65, as a result of which adjusting member 65 tries, somewhat, to rotate likewise. However, coil spring 95 and coupling 98 completely prevent rotation of adjusting member 65, during this rotation of the pre-selector wheel 56. Accordingly, only pre-selector wheel 56 rotates, to move numeral "4" into window 66.

(9) The patient had previously set the desired numeral "4" in the window 66. The patient now rotates the adjusting member 65 in the direction 99 (FIG. 6) or —the same thing—in direction 96 (FIG. 4).

Initially, manual rotation of adjusting member 65 is easy, because spring 59 fails to connect member 65 to pre-selector wheel 56.

This manual rotation of adjusting member 65 in direction 62 imparts rotation, likewise in direction 62, to plunger-lengthening mechanism 77.

For example: In step (8) above, pre-selector wheel 56 was turned from the "0" position to the "4" position. This amount of rotation was, for example, 40°

Now, in present step (9), the patient can rotate adjusting member 65 in direction 96 for 40°. After 40° of rotation, the right end 62 of spring 59 again comes to notch 58 of pre-selector wheel 56 and enters notch 58.

During this 40° of rotation of adjusting member 65, plunger-lengthening mechanism 77 turns, and plunger 18 moves out a corresponding distance from the proximal end of 77. In other words, the total length of elements 18+77 is increased from the prior, "zero" or null length to the length needed for 4 units of medication.

(9a) Also, during this 40° rotation of adjusting member 65, the numeral in window 66 goes from 4 to 3, from 3 to 2, etc. At the end of this 40° of rotation of adjusting member 65, the numeral in window 66 is again "0" (zero).

In this example of 40°, the patient cannot rotate the adjusting member 65 more than 40°. If the patient tries to rotate member 65 more than this 40°, the end 62 of spring 59 begins to try to rotate pre-selector wheel 56 in the same direction. However, as already mentioned, spring 59 of pre-selector wheel 56 is stron, and pre-selector wheel 56 is advantageously a little difficult to rotate. Therefore, if the patient tries to rotate the adjusting member 65 more than 40°, the patient will begin to feel the relatively strong resistance from the pre-selector wheel 56; therefore, he will know that he should not rotate adjusting member 65 further. Also, if the patient is very strong and e.g. in a hurry, and rotates the adjusting member 65 more than this 40°, he will hear a loud click noise: i.e., when spring end 53 falls down the next ratchet tooth 49. As a result, the patient will know that he has made a mistake, and that he must begin again.

If the designer feels that the just-described safety feature is not good enough, other possibilities exist. For example, an additional locking element, not shown, can be used. When the patient begins to turn adjusting member 65, a projection on member 65, for example, can move a spring, and the non-illustrated locking member can enter into a non-illustrated hole in pre-selector wheel 56, so that wheel 56 can be locked against rotation. Later, when the patient triggers the injection, the trigger mechanism can have a projection, to move such locking element away from the pre-selector wheel. Other possibilities will be evident.

(10) As said above, the patient has rotated the adjusting member 65 about 40° in direction 99 (FIG. 6) or —the same thing—direction 96 in FIG. 4. The injection device 10 is now ready to operate.

(11) The patient positions the proximal end of the injection device 10 against the correct part of his body. Then the patient presses the clip 11 inward.

As a result, the longitudinal guidance element 83 becomes unlocked. Drive spring 95 now pushes plunger-lengthening mechanism 77 and plunger 18 in the proximal direction at high speed. The head 18' of plunger 18 hits with high speed against the distal end of piston 17.

Two forces now resist further proximal movement of plunger 18 due to the force from drive spring 95. The first force is from needle return spring 29 and is comparatively weak. The second force is from the medication fluid at the proximal side of piston 17 and is comparatively strong, because the medicament must leave container 12 through needle 16, and this requires a certain amount of force and time.

Therefore, plunger 18 first presses fast against spring 29, and spring 29 is quickly compressed. As a result, the container-holding sleeve 20, the screw cap 25 at the distal end of 20, and the needle 16 at the proximal end of 20, move at high speed in the proximal direction; i.e. the proximal end of needle 16 enters at high speed into the body of the patient.

Next, the medicament (e.g. insulin) at the proximal side of piston 17 begins to exit the proximal end of needle 16, inside the tissue of the patient.

Accordingly, the volume of medicament at the proximal side of piston 17 continuously decreases during the injection. As a result, the spring-driven plunger 18 can move deeper and deeper into the container 12 during the injection.

When the plunger 18 moves out of the plunger-lengthening mechanism 77 the full distance (corresponding to the selected does of e.g. 4 units of insulin), the injection is finished.

The injection device 10 is pulled away from the patient, and the needle 16 leaves the patient's body. The spring 29 does not push the needle 16 back into the fron housing part 30. Instead, the needle 16 remains projected from the housing part 30.

(12) Therefore, in preparation for the next required injection, the old needle 16 is easily accessible and can be unscrewed and replaced by a fresh needle.

(13) The container 12, still having a considerable amount of insulin therein, can be used also for such next injection as well.

(14) Next, the patient rotates the handgrip 100 a small distance in direction 106 (FIG. 1) or —the same thing—direction 96 (FIG. 4). As a result, one drop 107 of fluid comes out of needle end 15. Therefore, the patient verifies that the total length of plunger 18 +plunger-lengthening mechanism 77 is the correct "zero" or null length for the next injection.

This is the same as step (5a) further above.

(15) Next, the patient pulls the handgrip in distal direction, to compress the spring 95 (as shown in FIG. 2). When the pawl nose 104 snaps into the window 42, the injection device is again cocked; drive spring 95 is loced in the compressed state of FIG. 2.

This step (15) is the same as step (6) above.

Next, the patient performs—again—steps (7) to (15) for the third injection and then—again—for the fourth injection, etc.

When the container 12 becomes empty or almost empty, the patient returns to step (1), etc.

At step (7) above, it is said that the numeral in window (66) will already be "0" (zero). Why this is true can be seen in step (9a) above.

Because injection of medicament into body tissue occurs only in a single direction of needle motion, it is substantially painless for the patient. Furthermore, the i injection can be performed with only one hand. Therefore, with the illustrated with the illustrated, preferred version of the inventive device, an injection can be performed even into the back of the patient or into the buttocks; i.e. more of the surface of the patient's body can be reached and be available for such an injection. This is very important in the case of intensivated insulin therapy with its substantially higher frequency of injection. Of course, adjustment of the injection device can also be performed in other ways: the handgrip 100 can be rotated correspondingly far in the direction of arrow 106; if that is done, then a corresponding scale of numerals (like the scale on extension 57) is advantageously provided between the housing part 32 and the handgrip 100. For the adjustment of an inventive injection device there are, as can be seen without further detailed elaboration, many other possibilities and modifications. The illustrated version—which is suitable especially for blind patients—is to be considered only as one of various possibilities.

In the foregoing description reference was mainly made to the injection of insulin. However, the injection device can of course be used in the same way for the injection of other substances, e.g. for the injection of hydroxocobalamin for anemia, the injection of pain killers in the case of cancer patients or, in the case of veterinary medicine, for mass inoculating of animals, one after the next in a large group.

Without further analysis, the foregoing will so fully reveal the gist of the present invention that others can, by applying current knowledge, readily adapt it for various modifications without omitting features that, from the standpoint of prior art, fairly constitute essential features of the generic or specific aspects of the invention.

We claim:

1. Injection device for performing dosed injections, said injection device defining a proximal end and a distal end, and having
    a housing (30, 32) for reception of an ampule or medication container (12) retaining a medicinal fluid, and a fluid expelling piston (17) movable in proximal direction within the ampule;
    an injection needle (16) engageable with the proximal end of the ampule and movable with the ampule in proximal direction with respect to the housing, in an injecting direction;
    an injection plunger (18) engageable against said piston (17);
    a plunger length setting mechanism (77) coupled to said plunger and forming with said plunger an injection dosing arrangement (18-77);
    a spring (95) coupled to the injection dosing arrangement (18-77);
    user operable spring cocking means (100);
    user operable spring release means (42, 104),
    said spring (95), after cocking, moving the plunger (18) of the injection dosing arrangement (18-77), upon release by the spring release means (41, 104) in engagement with said piston (17) to expel medicament fluid from the injection needle (16),
    wherein, in accordance with the invention,
    the plunger length setting mechanism (18-77) comprises
    a tubular element (77') having an internal thread;
    the injection plunger (18) includes an elongated stem (18") having an external thread (76) matching the internal thread of the tubular element (77) and telescopically receivable therein, and a plunger head (18') engageable with said piston (17) of the ampule;
    means (80, 82, 83) are provided for restraining relative rotation of the injection plunger (18) with respect to the housing (30, 32) while permitting axial movement of said injection plunger and said plunger length setting mechanism (77) within the housing; and
    user dosage setting means (56, 65) are provided and engageable with said tubular element (77') of the plunger length setting mechanism (77) to effect relative rotation of the plunger length setting mechanism (77) and to control the extent of telescopic penetration of the plunger (18) within said tubular element (77') and hence the overall length of the injection dosing arrangement (18-77) to thereby control the extent of movement of said piston (17) within the ampule upon release of said spring (95) by the spring release means (42, 104).

2. The device of claim 1, wherein said means for restraining relative rotation of the injection plunger (18) with respect to the housing comprises
    an at least partially essentially cylindrical guide element (83) formed with an axial opening therein;
    interengaging projection-and-recess means (80, 82) formed at the outside of said elongated stem (18") and at said elongated opening; and
    means (103, 104) formed on said guide element and coupling said guide element in rotation-inhibited manner to said housing (82).

3. The device of claim 2, wherein said interengaging projection-and-recess means, (80, 82) comprises an axially extending groove or slot (80) extending along said elongated stem (18") of the injection plunger; and
    an internal projection (82) extending into the opening formed in said guide element (83).

4. The device of claim 2, wherein said guide element (83) and said plunger length setting mechanism (77) are in engaged coupled relationship, permitting relative rotation of said plunger length setting mechanism (77) with respect to said guide element, while coupling said guide element and said plunger length setting mechanism (77) together for conjoint axial motion upon axial movement of said plunger length setting mechanism (77).

5. The device of claim 1, wherein said means for restraining relative rotation of the injection plunger (18) with respect to the housing comprises interengaging projection-and-recess means (103, 104, 40, 41) formed, respectively, within said housing and on said guide element.

6. The device of claim 5, wherein said projection-and-recess means comprises a projecting ridge (103) formed on said guide element;

and an internal groove (41) formed on the inside of the housing, slidably engageable by said projecting ridge.

7. The device of claim 1, wherein said internal and external threads within the tubular element (77') and on the stem (18") of the plunger (18), respectively, are steep-pitch spiral threads.

8. The device of claim 1, including coupling means coupling said user dosage setting means (56, 65, 100) to said plunger length setting mechanism (77).

9. The device of claim 8, wherein said user dosage setting means includes a hand grippable element (100) and a coupling arrangement for tensioning said spring (65) and thereby cocking said injection device.

10. The device of claim 1, further including coupling means coupling the user dosage setting means (56, 65, 100) with said plunger setting mechanism (77), said coupling means (98) comprising at least one of:
a slip or friction coupling;
a one-way of free-wheel coupling;
a torsion or spiral spring coupling.

11. The device of claim 1, wherein said spring (95) comprises a spiral spring coupled to and acting on the tubular element (77') of the injection dosing arrangement.

12. The device of claim 1, wherein said user operable spring cocking means comprises a latch means (42, 104) retaining the spring (95) and said injection dosing arrangement (18–77) in cocked position;
and wherein said user operable spring release means comprises a release (11) to unlatch said latch means.

13. The device of claim 12, wherein said latch means comprises an opening (42) formed in the housing (32) of the device and an engagement projection (104) fitting into said opening and coupled to said injection dosing arrangement (18–77).

14. The device of claim 13, wherein said housing (32) includes an inner axially extending longitudinal groove or slot (41);
and wherein said projection (104) is slidable within said groove or slot.

15. The device of claim 14, wherein said means for restraining relative rotation of the injection plunger (18) with respect to the housing comprises
an at least partially essentially cylindrical guide element (83) formed with an axial opening therein;
interengaging projection-and-recess means (80, 82) formed at the outside of said elongated stem (18") and at said elongated opening;
means (103, 104) formed on said guide element and coupling said guide element in rotation-inhibited manner to said housing (82);
and wherein said projecting (104) is formed on said guide element (83) at a side thereof remote from said opening, and fitting into said groove or slot (41), and providing for longitudinal guidance of said guide element within said housing while restraining said guide element from relative rotation with respect to said housing.

16. The device of claim 1, wherein said dosage setting means (56, 65) includes a ratchet means (48, 49; 52, 53, 54; 56, 55) having a spring (52) which snaps over ratchet teeth (49) of the ratchet means to provide an audible signal upon rotation of said dosage setting means.

17. The device of claim 16, wherein said dosage setting means (56, 65) includes indicating means (57, 66) for visually indicating a selected dosage.

18. The device of claim 1, wherein said user operable dosage setting means comprises a preselection element (56) and positionable with respect to said housing.

19. The device of claim 18, wherein said user operable dosage setting means further includes a setting element (65);
said preselecting element (56) having an abutment means (58), said setting element being settable on said housing and engageable with said abutment means for positioning the setting element in accordance with the setting of the preselecting element and hence the position of said abutment means (58);
and coupling means (98) coupling the setting element with said injection dosing arrangement (18–77) to control the combined length of the injection plunger (18) and the plunger length setting mechanism (77) and hence the dosage to be injected.

20. The device of claim 19, wherein said housing (30, 32) comprises an elongated, essentially cylindrical structure;
and said preselecting element (56) and said setting element (65), each, are ring means coaxial with, and on said housing.

21. The device of claim 1, further including a return spring (29) located within said housing and coupled to said ampule or medication containing container (12) and resiliently biassing said ampule or medication containing container (12) in a distal direction.

22. The device of claim 1, further including a reception sleeve (20) located within the housing and dimensioned and shaped to receive an ampule or medication containing container (12);
and a return spring (29) located within the housing and biassing said reception sleeve (20) in distal direction,
said reception sleeve being movable counter the force of said return spring in proximal direction under force of said injection spring (95).

23. The device of claim 1, wherein said tubular element (77') having the internal thread is positioned within said housing for relative axial displacement between a predetermined proximal and position and a predetermined distal end position.

24. The device of claim 23, wherein said spring (95) is positioned between an inner wall of the housing and the outside of said tubular element (77'), and
said spring being stressed or cocked upon shifting of said tubular element (77') in said predetermined distal end position.

25. Injection device for performing dosed injections, said injection device defining a proximal end and a distal end, and having
a housing (30, 32) for reception of an ampule or medication container (12) retaining a medicinal fluid, and a fluid expelling piston (17) movable in proximal direction within the ampule;
an injection needle (16) engageable with the proximal end of the ampule and movable with the ampule in proximal direction with respect to the housing, in an injecting direction;
an injection plunger (18) engageable against said piston (17);

a plunger length setting mechanism (77) coupled to said plunger and forming with said plunger an injection dosing arrangement (18-77);

a spring (95) coupled to the injection dosing arrangement (18-77);

user operable spring cocking means (100);

user operable spring release means (42, 104), said spring (95), after cocking, moving the plunger (18) of the injection dosing arrangement (18-77), upon release by the spring release means (41, 104) in engagement with said piston (17) to expel medicament fluid from the injection needle (16), wherein, in accordance with the invention, the plunger length setting mechanism (18-77) comprises a tubular element (77') having an internal thread;

the injection plunger (18) includes an elongated stem (18") having an external thread (76) matching the internal thread of the tubular element (77) and telescopically receivable therein;

a guide element (83) guiding said elongated stem (18"), and interengaging projection-and-recess means (82, 80) formed on said guide element and said elongated stem, respectively, to prevent relative rotation of the guide element and the plunger (18) while permitting relative axial movement of the guide element and said plunger;

means (103, 104) for coupling the guide element (83) with the housing (32) of the device while preventing relative rotation of the guide element and the housing; and user operable setting means (56, 65, 100) coupled to the tubular element (77') of the plunger length setting mechanism for causing and controlling relative rotation (106) between said guide element (83) and said plunger length setting mechanism (77) to selectively control and change the overall length of said injection dosing arrangement (18-77) in accordance with the selected injection dosage.

26. The device of claim 25, wherein said user dosage setting means includes a user operable element (100) coupled to said tubular element (77') of the plunger length setting mechanism (77).

27. The device of claim 25, wherein said guide element is coupled to said plunger length setting mechanism (77) for axial movement with said plunger length setting mechanism while permitting relative rotation of said plunger length setting mechanism and said guide element.

28. The device of claim 25, wherein said internal and external threads within the tubular element (77') and on the stem (18") of the plunger (18), respectively, are steep-pitch spiral threads.

29. The device of claim 25, wherein said tubular element having the internal thread is positioned within said housing for relative axial displacement between a predetermined proximal end position and a predetermined distal end position.

30. The device of claim 29, wherein said spring (95) is positioned between an inner wall of the housing and the outside said tubular element (77'), and said spring being stressed or cocked upon shifting of said tubular element (77') in said predetermined distal end position.

31. In an injection device for injecting fluid medication from an ampule or container (12) having an ejection piston (17) for injecting the medication through a needle (16) coupled to the container upon axial movement of the piston, means for moving said piston including an injection dosing arrangement (18-77) of adjustable length, said injection dosing arrangement having a tubular element (77') formed with an inner thread, and a plunger means (18) having an elongated stem (18") formed with an external thread (76) matching said internal thread of the tubular element, said plunger means being engageable with the piston (17) in said ampule or container (12), comprising, in accordance with the invention, a guide element (83) rotatably coupled to said tubular element;

a groove or slot (80) extending in axial direction formed in said elongated stem (18");

projecting means (82) on said guide element (83) engageable with said groove or slot (80);

interengaging projection-and-recess means (103, 104; 41) formed on said coupling element (83) and interiorly of a housing (32) of said device to permit relative longitudinal movement of said guide element within the housing while preventing relative rotation of the guide element (83) with respect to the housing (32); and means (65, 100) for rotating said internally threaded tubular element (77), whereby, upon rotation of said tubular element, said plunger means (18) will telescopically move into or out of said tubular element while being guided longitudinally within said housing.

32. The device of claim 31, wherein said internal and external threads within the tubular element (77') and on the stem (18") of the plunger (18), respectively, are steep-pitch spiral threads.

33. The device of claim 31, further including an injection spring (95) operatively coupled to said injection dosing arrangement (18-77) and positioned for resiliently stressing said injection dosing arrangement (18, 77);

latching means for retaining the spring in stressed condition; and stress release means acting on said latch means to permit relaxation of the stressed spring and thereby moving said injection dosing arrangement (18-77) in injecting direction against said piston (7).

34. The device of claim 33, wherein said injection spring (95) comprises a spiral spring surrounding said tubular element (77');

and user operable rotary setting means engageable with one end of said spiral spring, rotation of said setting means transferring rotation to said tubular element when rotated in wind-up direction of the spiral spring, but not transferring rotation when rotated in an opposite direction, whereby said spring will have the dual function of a one-way engagement clutch as well as an injection effecting spring for said injection dosing arrangement (18-77).

35. The device of claim 31, wherein said tubular element having the internal thread is positioned within said housing for relative axial displacement between a predetermined proximal end position and a predetermined distal end position.

36. The device of claim 35, wherein said spring (95) is positioned between an inner wall of the housing and the outside said tubular element (77'), and said spring being stressed or cocked upon shifting of said tubular element (77') in said predetermined distal end position.

37. In an injection device for injecting fluid medication from an ampule or container (12) having
   a housing for reception of said ampule or container (12);
   an ejection piston (17) for ejecting the medication through a needle (16);
   means for moving said piston (17) including an axially movable injection dosing arrangement (18, 77') of adjustable length, said injection dosing arrangement having
      a tubular element (77') formed with an inner thread, and a plunger means (18) having an elongated stem (18") formed with an external thread (76) matching said internal thread of said tubular element (77'),
   said plunger means being engageable with the piston (17) in said ampule or container (12),
   comprising, in accordance with the invention,
   means (80, 82, 83, 104) for restraining relative rotation of said plunger means (18) with respect to the housing (30) while permitting axial movement of said plunger means (18) within said housing (30); and
   user dosage setting means (56, 65) to effect relative rotation between said housing (30) and said tubular element (77') to control the amount of telescopic extension of said plunger means (18) from said tubular element (77') and hence the overall length of said injection dosing arrangement (18, 77').

38. The device of claim 37, wherein said internal and external threads within the tubular element (77') and on the stem (18") of the plunger (18), respectively, are steep-pitch spiral threads.

39. The device of claim 37, further including an injection spring (95) operatively coupled to said injection dosing arrangement (18-77) and positioned for resiliently stressing said injection dosing arrangement (18, 77);
   latching means for retaining the spring in stressed condition; and
   stress release means acting on said latch means to permit relaxation of the stressed spring and thereby moving said injection dosing arrangement (18-77) in injecting direction against said piston (7).

40. The device of claim 39, wherein said injection spring (95) comprises a spiral spring surrounding said tubular element (77');
   and user operable rotary setting means engageable with one end of said spiral spring, rotation of said setting means transferring rotation to said tubular element when rotated in wind-up direction of the spiral spring, but not transferring rotation when rotated in an opposite direction, whereby said spring will have the dual function of a one-way engagement clutch as well as an injection effecting spring for said injection dosing arrangement (18-77).

41. The device of claim 37, wherein said tubular element (77') having the internal thread is positioned within said housing for relative axial displacement between a predetermined proximal end position and a predetermined distal end position.

42. The device of claim 41, wherein said spring (95) is positioned between an inner wall of the housing and the outside of said tubular element (77'), and
   said spring being stressed or cocked upon shifting of said tubular element (77') in said predetermined distal end position.

* * * * *